United States Patent [19]
Ahmadi

[11] Patent Number: 5,163,906
[45] Date of Patent: Nov. 17, 1992

[54] DILATATION CATHETER AND METHOD FOR WIDENING OF STRICTURES

[75] Inventor: Ramazan-Ali Ahmadi, Vienna, Austria

[73] Assignee: Schneider (Europe) AG, Bulach, Switzerland

[21] Appl. No.: 851,226

[22] Filed: Mar. 12, 1992

Related U.S. Application Data

[63] Continuation of Ser. No. 744,646, Aug. 8, 1991, abandoned, which is a continuation of Ser. No. 411,937, Sep. 25, 1989, abandoned.

[30] Foreign Application Priority Data

Sep. 27, 1988 [CH] Switzerland ............... 3584/88

[51] Int. Cl.$^5$ ............................................. A61M 29/00
[52] U.S. Cl. ..................................... 604/101; 606/194
[58] Field of Search .......................... 604/96–103; 606/191, 194; 128/898

[56] References Cited

U.S. PATENT DOCUMENTS

| | | | |
|---|---|---|---|
| 4,230,108 | 10/1980 | Young | 604/101 |
| 4,423,725 | 1/1984 | Baran et al. | 604/101 |
| 4,573,966 | 3/1986 | Weikl et al. | 604/101 |
| 4,610,662 | 9/1986 | Weikl et al. | 604/101 |
| 4,655,746 | 4/1987 | Daniels et al. | 604/101 |
| 4,664,114 | 5/1987 | Ghodsian | 604/101 |
| 4,696,668 | 9/1987 | Wilcox | 604/101 |
| 4,705,502 | 11/1987 | Patel | 604/101 |
| 4,930,496 | 6/1990 | Bosley, Jr. | 604/101 |
| 4,932,958 | 6/1990 | Reddy et al. | 604/101 |

Primary Examiner—C. Fred Rosenbaum
Assistant Examiner—William W. Lewis
Attorney, Agent, or Firm—Peter C. Richardson; Lawrence C. Akers; John L. LaPierre

[57] ABSTRACT

A dilatation catheter intended in particular for treatment of strictures in the carotid artery has at its front end a dilatation balloon, which is inserted in the folded state into the carotid artery and is inflated in order to widen the stricture. In front of the dilatation balloon a sealing balloon is arranged which serves to seal off the carotid artery downstream of the stricture, in order thereby to prevent a migration of any stricture material which may become detached during treatment, and thus to avoid the risk of an embolism. Between the dilatation balloon and the sealing balloon there is a draw-off and inlet opening through which, after widening and with the sealing balloon inflated, detached stricture material can be drawn off or washed away.

8 Claims, 2 Drawing Sheets

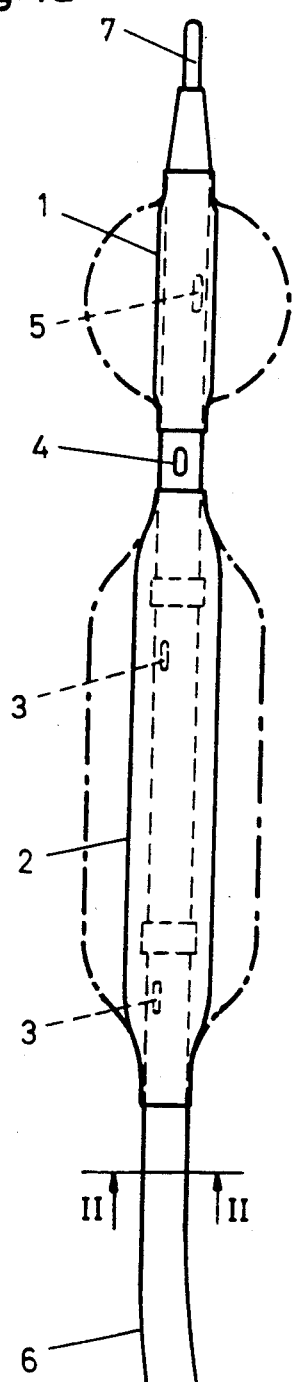
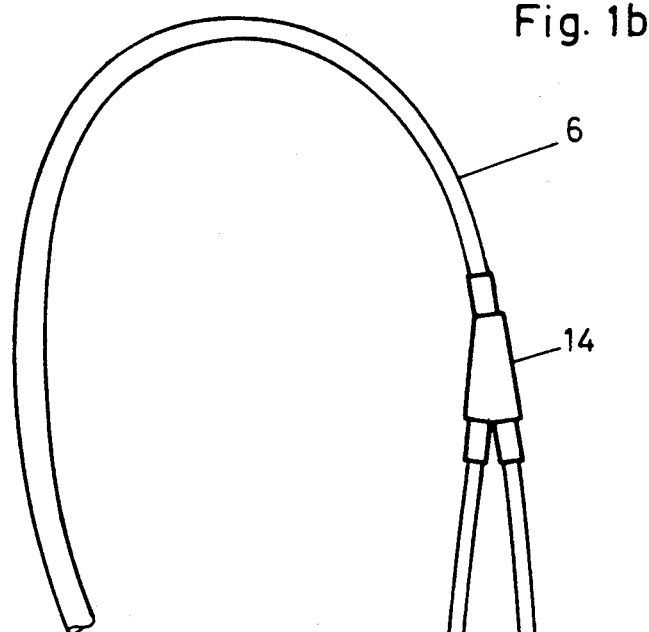
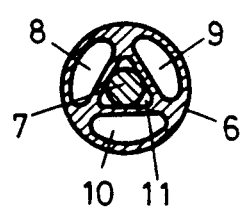
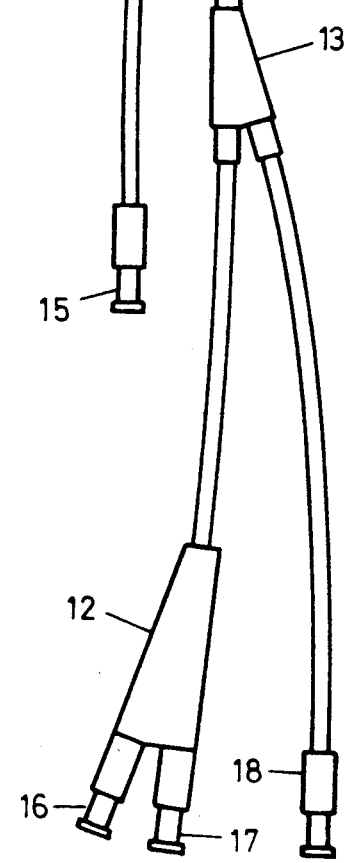

5,163,906

DILATATION CATHETER AND METHOD FOR WIDENING OF STRICTURES

This is a continuation of application Ser. No. 744,646, filed on Aug. 8, 1991, which is a continuation of application Ser. No. 411,936, filed on Sep. 25, 1989, now both abandoned.

BACKGROUND OF THE INVENTION

The invention relates to a dilatation catheter for the widening of a stricture in a blood vessel comprising a dilatation balloon arranged on a support tube and extensible up to a defined extent by means of an external pressure/suction pump to be connected to the support tube.

Dilatation catheters of this type are generally known and are used in particular for the widening of strictures in the arterial system. Such conventional dilatation catheters could not be used for treating strictures (stenoses) in the carotid artery on account of the high risk of an embolism. Therefore, in the treatment of strictures in the carotid artery, the comparatively mild treatment with a catheter has hitherto had to be dispensed with.

SUMMARY OF THE INVENTION

It is an object of the present invention to provide a dilatation catheter of the above type, which is particularly suitable for the widening of stenoses in the carotid artery. The dilatation catheter is designed in such a way that treatment involves the least possible risk and can be carried out safely and in a manner which does not impose strain on the patient.

This object is achieved by the present invention, in which the catheter further comprises an externally and elastically extensible sealing balloon spaced distally from the dilatation balloon and adapted to seal off the blood vessel distally of the stricture, and a draw-off and inlet opening is provided in the support tube between the dilatation balloon and the sealing balloon through which detached stricture material can be drawn off or fluid can be introduced. The dilatation catheter can be inserted into the vessel to be treated in a known manner by means of a guide wire. By means of the sealing balloon it is possible to seal the vessel off downstream of the stricture viewed in the direction of flow of the blood, in such a way that none of the particles, which may possibly become detached during treatment of the stricture, can be carried away. In this way the risk of an embolism is avoided. After the vessel is sealed off, the stricture can be widened mechanically by means of the dilatation balloon in a manner known per se. Here, detached particles remain in the area of the stricture and, after treatment of the stricture, can be completely removed or washed away through the draw-off and inlet device arranged between the two balloons. Advantageous further developments are described hereinbelow.

DETAILED DESCRIPTION OF THE INVENTION

An exemplary embodiment of the invention is illustrated in greater detail below with reference to the drawings, in which:

FIG. 1a shows, on an enlarged scale, a side view of the front part of a dilatation catheter according to the invention;

FIG. 1b shows a side view of the rear part of the dilatation catheter;

FIG. 2 shows a cross-section through the dilatation catheter along the line II—II in FIG. 1.

Figure 3A:
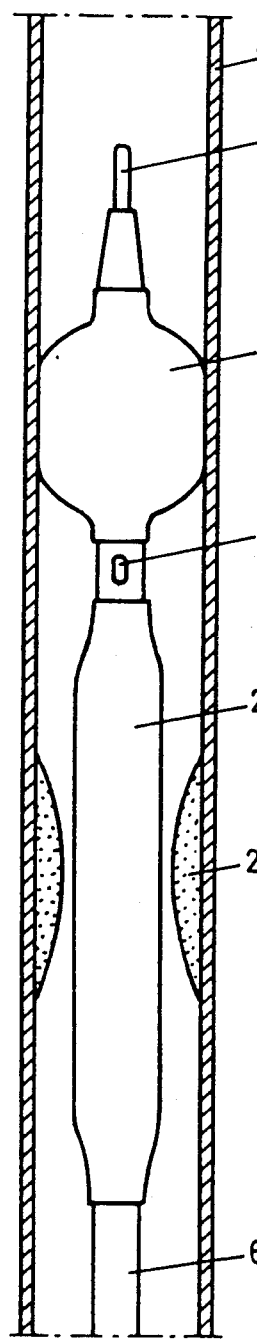
FIGS. 3a to 3d show a diagrammatic representation of a section of the carotid artery, with the front part of the catheter inserted therein, in different phases during treatment of a stricture.
Figure 3B:
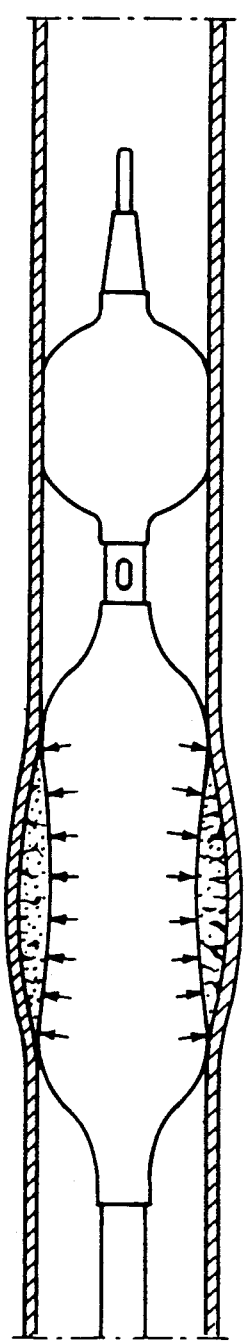

The dilatation catheter depicted in the drawings has a flexible support tube 6 with a continuous central channel 11 for receiving a likewise flexible guide wire 7. With the aid of the guide wire 7, the front end of the dilatation catheter can be pushed forwards to a longitudinal position 20 in the vessel 19 to be treated. In order to widen the stricture 20, there is arranged on the support tube 6 a dilatation balloon 2 which is folded during insertion of the catheter and which can be adjustably inflated up to a defined extent by means of a pressure/suction pump (not shown here) to be connected at a nipple 16. The pressure/suction pump is connected to the interior space of the dilatation catheter via a pressure channel 8, which terminates with openings 3 in the interior space. For X-ray positioning of the dilatation balloon 2, two metallic rings are arranged on the support tube 6. It is essential that the dilatation balloon 2 has a very slight elasticity at the pressures customary here and cannot be extended beyond the said defined extent.

In front of the dilatation balloon 2 and at a distance from it a sealing balloon 1 is arranged which, in the rest position, bears tightly on the support tube 6. This balloon is approximately 1 to 2 cm long and is firmly connected at its two ends to the support tube 6, for example welded on the support tube. In contrast to the dilatation balloon 2, this sealing balloon 1 is rubber-elastic and can be expanded with extension of its wall. The sealing balloon 1 is preferably made of latex. By means of a pressure/suction pump (not shown here), the sealing balloon 1 can be adjustably inflated into the spherical shape shown by dot-and-dash lines FIG. 1a. This pressure/suction pump is joined at the nipple 18 and is connected to the interior space of the sealing balloon 1 via a pressure channel 9. The channel 9 leads into this interior space via an opening 5 in the support tube 6.

Between the sealing balloon 1 and the dilatation balloon 2, the support tube 6 has a draw-off/inlet opening 4 which opens directly into the vessel 19 and leads via a channel 10 to a nipple 15 which is to be connected to a draw-off/inlet device (also not shown here). Particles which have become detached from the stricture during widening thereof can be drawn off or washed away through this draw-off/inlet opening during and after treatment.

From the openings 3 to a branch 14 the support tube 6 has four lumens, from this branch point 14 to the branch point 13 it has three lumens, and on the rearmost stretch up to branch piece 12 it has two lumens. The nipples 15 and 18 are connected to the corresponding branch positions via single-lumen tube sections. The channels to the openings 3, 4 and 5 are separate, so that the two balloons 1 and 2 can be inflated independently of each other, and material can be drawn off or let in through the opening 4 independently of the state of these balloons.

The use of the dilatation catheter is illustrated in greater detail with reference to FIGS. 3a to 3d.

The front end of the dilatation catheter is pushed forwards to the stricture 20 in the vessel 19 with the aid of the guide wire 7. The dilatation balloon 2 is folded during this step, and the sealing balloon 1 lies unstressed on the support tube 6. When the dilatation balloon 2 has been positioned, the sealing balloon 1 is inflated to such an extent that it bears on the inner side of the vessel 19 and seals the latter off to such an extent that no more body fluid can flow through at this point. This state is shown in FIG. 3a, where it can also be clearly seen that the soft and rubber-elastic sealing balloon 1 has come to bear sealingly on the vessel 19 without significant extension of the latter.

In the next step the dilatation balloon 2 is inflated and, as its size increases, it widens the stricture 20, which generally consists of spongy, calcium-rich and fat-rich tissue. By means of this widening, the tissue forming the stricture is partially pressed into the vessel wall.

Figure 3C:
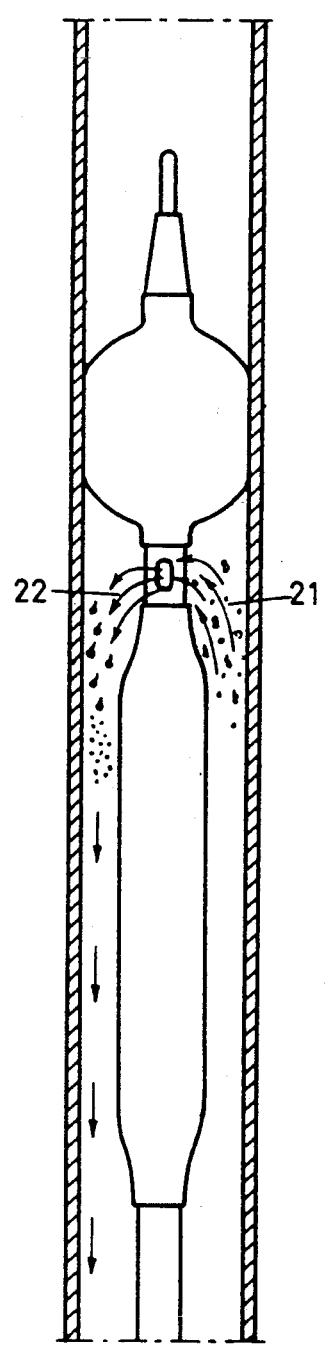
Figure 3D:
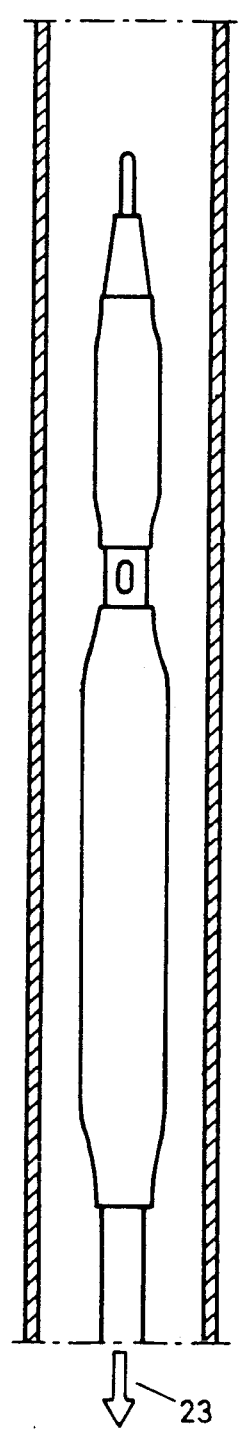

Now, as shown in FIG. 3c, the dilatation balloon 2 is brought into the contracted shape, and, at the same time or shortly before, body fluid and with it any detached stricture material is removed from the vessel 19 through the draw-off/inlet opening 4 in the direction of the arrows 21 and/or washed away in the direction of the arrows 22 (FIG. 3c). Finally, the sealing balloon 1 is returned to the unstressed form shown in FIG. 3d, and the catheter and the guide wire 7 are removed from the vessel 19. Individual treatment stages can of course also be repeated several times.

The treatment catheter according to the invention is suitable in particular for the treatment of strictures in the carotid artery.

I claim:

1. A method of widening a stricture in a blood vessel, the method comprising:
   a) providing a dilatation catheter comprising an elongated dilatation balloon arranged on a support tube and extensible up to a defined extent by means of an external pressure/section pump connected to the support tube, and a sealing balloon arranged on the support tube in the axial direction distally of and at a distance from the dilatation balloon, the wall of which sealing balloon is elastically extensible by means of an external pressure/suction pump connected to the support tube to seal off the vessel distally of the structure, with a draw-off and inlet opening being provided in the support tube distal to the dilatation balloon and proximal to the sealing balloon, said opening being of a size sufficient to accommodate detached structure material which can be drawn off to the exterior of the catheter or through which a washing fluid can be introduced;
   b) positioning the dilatation catheter at the site of a stricture so that the sealing balloon is situated distally of the stricture and the dilatation balloon is situated within the stricture;
   c) inflating the sealing balloon to an extent sufficient to seal off the vessel distally of the stricture;
   d) inflating the dilatation balloon to an extent sufficient to widen the stricture;
   e) drawing off any detached stricture material through the opening while simultaneously or immediately thereafter deflating the dilatation balloon; and
   f) deflating the sealing balloon and removing the dilatation catheter from the site of the stricture.

2. A method of widening a stricture in a blood vessel as claimed in claim 1 wherein the sealing balloon of the dilatation catheter has a rubber-elastic wall.

3. A method of widening a stricture in a blood vessel as claimed in claim 2 wherein the sealing balloon of the dilatation catheter is made of latex.

4. A method of widening a stricture in a blood vessel as claimed in claim 1 wherein the sealing balloon of the dilatation catheter bears upon the support tube in its rest position.

5. A method of widening a stricture in a blood vessel as claimed in claim 2 wherein the sealing balloon of the dilatation catheter is spherical when freely inflated.

6. A method of widening a stricture in a blood vessel as claimed in claim 1 wherein the dilatation balloon and the sealing balloon of the dilatation catheter are inflatable independent of each other via separate channels provided in the support tube.

7. A method of widening a stricture in a blood vessel as claimed in claim 1 wherein the sealing balloon of the dilatation catheter is radially extensible beyond the defined extent of the dilatation balloon thereof.

8. A method of widening a stricture in a blood vessel as claimed in claim 1 wherein the support tube of the dilatation catheter is provided with four lumens, including a central channel provided for receiving a guidewire.

* * * * *